United States Patent
Kawajiri

(10) Patent No.: US 12,357,253 B2
(45) Date of Patent: Jul. 15, 2025

(54) MEDICAL IMAGE DIAGNOSIS SYSTEM AND MEDICAL IMAGE DIAGNOSIS APPARATUS CONTROLLING METHOD

(71) Applicant: CANON MEDICAL SYSTEMS CORPORATION, Otawara (JP)

(72) Inventor: Sho Kawajiri, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 283 days.

(21) Appl. No.: 17/343,054

(22) Filed: Jun. 9, 2021

(65) Prior Publication Data

US 2021/0393223 A1     Dec. 23, 2021

(30) Foreign Application Priority Data

Jun. 22, 2020   (JP) ................. 2020-107220

(51) Int. Cl.
| | | |
|---|---|---|
| A61B 5/00 | (2006.01) | |
| A61B 5/055 | (2006.01) | |
| A61B 6/00 | (2006.01) | |
| A61B 6/03 | (2006.01) | |
| A61B 6/04 | (2006.01) | |
| A61B 6/46 | (2024.01) | |

(52) U.S. Cl.
CPC .............. *A61B 6/488* (2013.01); *A61B 5/055* (2013.01); *A61B 6/032* (2013.01); *A61B 6/0407* (2013.01); *A61B 6/461* (2013.01); *A61B 6/467* (2013.01); *A61B 6/54* (2013.01)

(58) Field of Classification Search
CPC ......... A61B 6/032; A61B 5/055; A61B 8/461; A61B 6/488; A61B 6/0407
See application file for complete search history.

(56) References Cited

U.S. PATENT DOCUMENTS

2002/0152107 A1* 10/2002 Mifune .............. G06Q 10/1097
                                                        705/7.19
2008/0208048 A1*  8/2008 Maruyama ............... A61B 8/06
                                                        600/437

(Continued)

FOREIGN PATENT DOCUMENTS

JP      2001-052088 A     2/2001
JP      2008-54749 A      3/2008

(Continued)

OTHER PUBLICATIONS

Combined Chinese Office Action and Search Report issued Jul. 6, 2023 in Patent Application No. 202110684233.8 (with English translation of Category of Cited Documents), 8 pages.

(Continued)

*Primary Examiner* — Joel F Brutus
(74) *Attorney, Agent, or Firm* — Oblon, McClelland, Maier & Neustadt, L.L.P.

(57) ABSTRACT

A medical image diagnosis system according to an embodiment includes a sensor and a processing circuitry. The sensor is configured to detect whether or not a mobile terminal is mounted on a mount base capable of having the mobile terminal mounted thereon. The processing circuitry is configured, when it is detected that the mobile terminal is mounted on the mount base, to exercise control over a medical image diagnosis apparatus.

15 Claims, 9 Drawing Sheets

(56) References Cited

U.S. PATENT DOCUMENTS

| | | | | |
|---|---|---|---|---|
| 2009/0141854 | A1* | 6/2009 | Hirokawa | A61B 6/542 |
| | | | | 378/4 |
| 2014/0074493 | A1* | 3/2014 | Schneider | G16H 15/00 |
| | | | | 340/5.82 |
| 2015/0168513 | A1* | 6/2015 | Mori | G01R 33/34 |
| | | | | 324/322 |
| 2018/0355482 | A1* | 12/2018 | Chen | C23C 16/45551 |
| 2019/0086499 | A1* | 3/2019 | Ohishi | G01R 33/385 |
| 2019/0200942 | A1* | 7/2019 | DeFreitas | A61B 6/502 |
| 2020/0367851 | A1* | 11/2020 | Gotanda | A61B 6/5205 |
| 2021/0393231 | A1* | 12/2021 | Nishijima | G06N 3/08 |
| 2022/0101993 | A1* | 3/2022 | Zhang | G16H 40/67 |
| 2022/0206098 | A1* | 6/2022 | Leussler | G01R 33/5673 |

FOREIGN PATENT DOCUMENTS

| | | |
|---|---|---|
| JP | 2010-115478 A | 5/2010 |
| JP | 2014-200378 A | 10/2014 |
| JP | 2020-65631 A | 4/2020 |

OTHER PUBLICATIONS

Japanese Office Action issued Oct. 17, 2023 in Japanese Patent Application No. 2020-107220, 2 pages.

Japanese Office Action dated Feb. 13, 2024, in Japanese Patent Application No. 2020-107220, 2 pages.

* cited by examiner

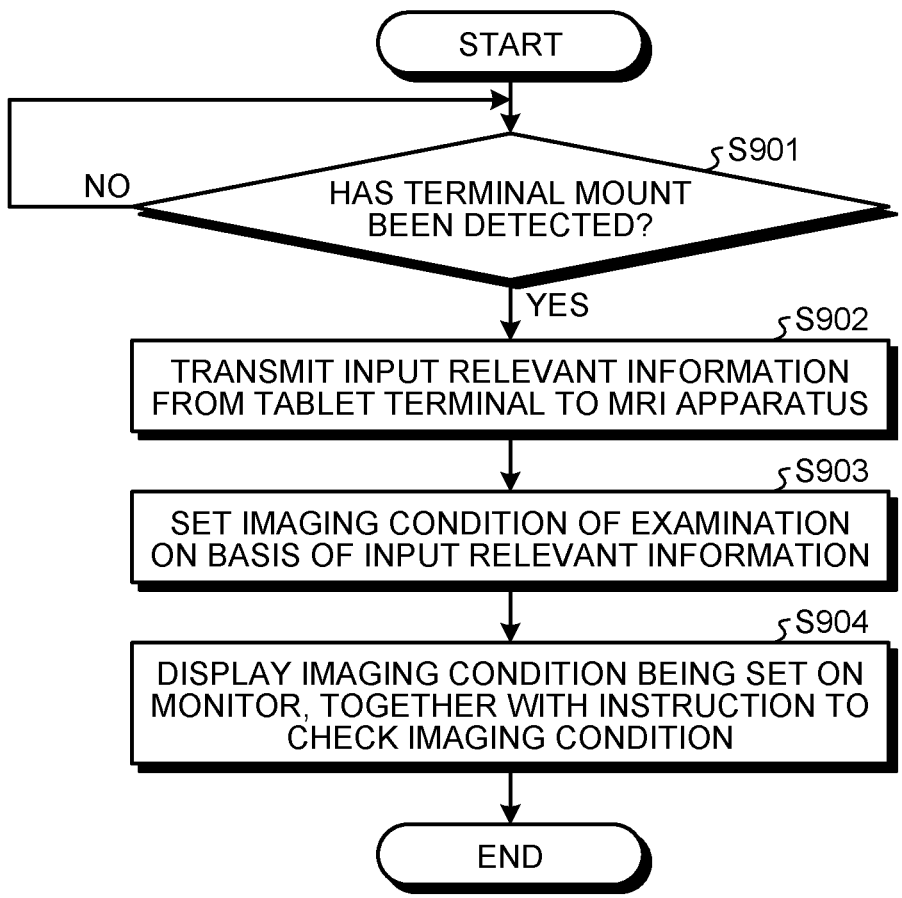

MEDICAL IMAGE DIAGNOSIS SYSTEM AND MEDICAL IMAGE DIAGNOSIS APPARATUS CONTROLLING METHOD

CROSS-REFERENCE TO RELATED APPLICATIONS

This application is based upon and claims the benefit of priority from Japanese Patent Application No. 2020-107220, filed on Jun. 22, 2020; the entire contents of which are incorporated herein by reference.

FIELD

Embodiments described herein relate generally to a medical image diagnosis system and a medical image diagnosis apparatus controlling method.

BACKGROUND

Before imaging an examined subject (hereinafter, "patient"), a user (e.g., a technologist) may input information necessary for the imaging to a medical image diagnosis apparatus installed in an imaging room, by using a mobile terminal such as a tablet. When the mobile terminal and the medical image diagnosis apparatus are configured to work in conjunction with each other, the user (e.g., the technologist) guides the patient to the medical image diagnosis apparatus while carrying the mobile terminal around. The mobile terminal carried around by the user (e.g., the technologist) may get in the way while the user (e.g., the technologist) is guiding the patient. Carrying around the mobile terminal may make it difficult for the user (e.g., the technologist) to assist the patient before the imaging, e.g., to provide guidance while placing the patient on a couch.

For this reason, the medical image diagnosis apparatus using the mobile terminal may have a low throughput of medical examinations.

BRIEF DESCRIPTION OF THE DRAWINGS

FIG. 9 is a flowchart illustrating an example of a flow in a condition setting checking process according to the fourth embodiment.

DETAILED DESCRIPTION

Exemplary embodiments of a medical image diagnosis system, a medical image diagnosis apparatus controlling program, and a medical image diagnosis apparatus will be explained in detail below, with reference to the accompanying drawings. The medical image diagnosis system includes a medical image diagnosis apparatus, a mobile terminal, and a mount unit capable of having the mobile terminal mounted thereon. The mobile terminal does not necessarily have to be a dedicated terminal accompanying the medical image diagnosis apparatus and may be realized by, for example, wireless hardware such as a tablet terminal or a smartphone possessed by an in-hospital worker (a user) such as a medical doctor or a technologist.

In this situation, the mobile terminal does not necessarily have to be a terminal capable of wirelessly communicating with the medical image diagnosis apparatus and may be a terminal incapable of wirelessly communicating with the medical image diagnosis apparatus. In that situation, the mount unit may have a function of realizing communication between the mobile terminal and the medical image diagnosis apparatus. Further, a monitoring device (not illustrated) different from the mobile terminal and the mount unit may be configured to monitor whether or not the mobile terminal is mounted on the mount unit so that, when being triggered by detecting that the mobile terminal is mounted on the mount unit, either the monitoring device or another wireless connection device establishes a wireless connection between the mobile terminal and the medical image diagnosis apparatus. In the following sections, to explain specific examples, the mobile terminal according to certain embodiments is assumed to be a tablet terminal capable of communicating with the medical image diagnosis apparatus via the mount unit.

The medical image diagnosis apparatus included in the medical image diagnosis system corresponds to any of various types of modalities such as an X-ray Computed Tomography apparatus (hereinafter, "X-ray CT apparatus"), an X-ray diagnosis apparatus, a magnetic resonance imaging apparatus (hereinafter, "MRI apparatus"), a nuclear medicine diagnosis apparatus, or an ultrasound diagnosis apparatus.

In the following sections, to explain specific examples, the medical image diagnosis apparatus is assumed to be an MRI apparatus. Other examples in which the medical image diagnosis apparatus in the medical image diagnosis system is a different modality will be explained as appropriate.

EMBODIMENTS

A medical image diagnosis system according to an embodiment includes a detecting unit and a controlling unit. The detecting unit is configured to detect whether or not a mobile terminal has been mounted on a mount unit capable of having the mobile terminal mounted thereon. When it is detected that the mobile terminal is mounted on the mount unit, the controlling unit is configured to exercise control over the medical image diagnosis apparatus.

Figure 1:
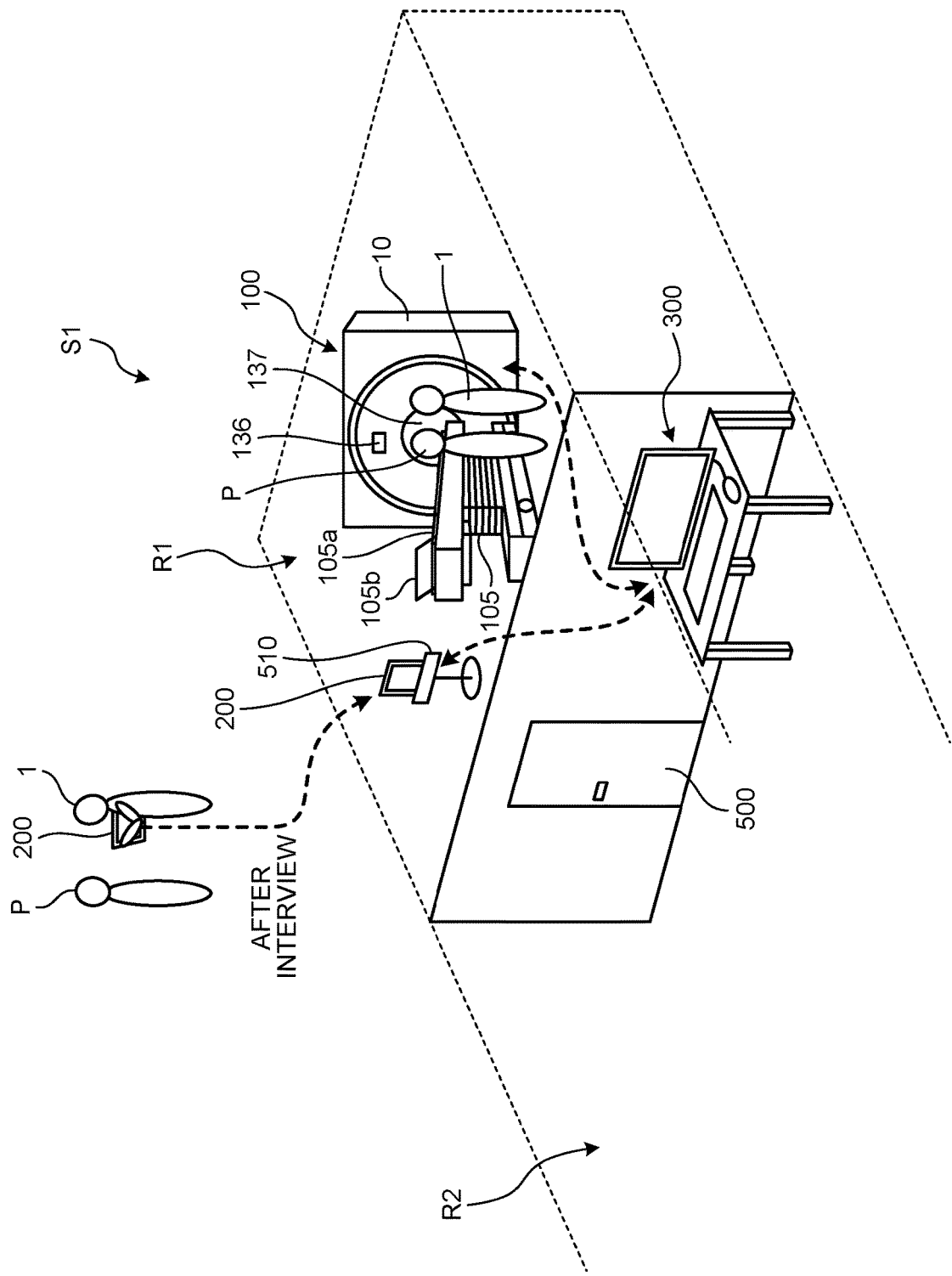
FIG. 1 is a drawing illustrating an example of an imaging room in which a Magnetic Resonance Imaging (MRI) apparatus included in a medical image diagnosis system according to a first embodiment is installed.
Figure 2:
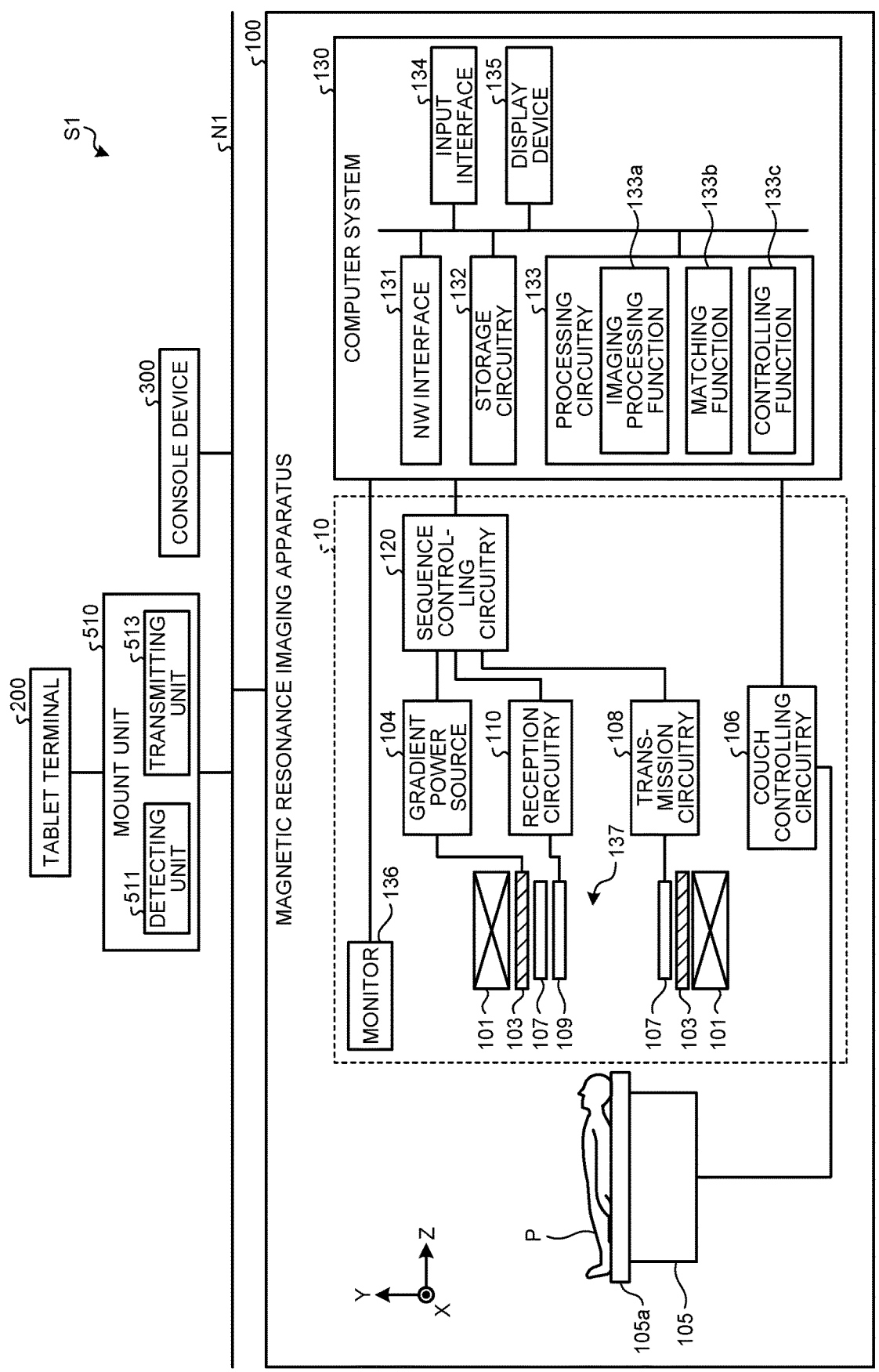
FIG. 2 is a block diagram illustrating an example of the medical image diagnosis system including the magnetic resonance imaging apparatus according to the first embodiment.

FIG. 1 is a drawing illustrating an example of an imaging room R1 in which an MRI apparatus 100 included in a medical image diagnosis system S1 according to a first embodiment is installed. As illustrated in FIG. 1, the medical image diagnosis system S1 includes the MRI apparatus 100, a tablet terminal 200 realized with a mobile terminal, and a mount unit 510 capable of having the tablet terminal 200 mounted thereon. Further, the medical image diagnosis system S1 may further include other constituent elements such as the monitoring device described above. FIG. 2 is a block diagram illustrating an example of the medical image diagnosis system S1 including the MRI apparatus 100 according to the first embodiment.

By implementing magnetic resonance imaging, the MRI apparatus 100 is configured to image a patient P. For example, the patient P corresponds to a patient undergoing a medical examination (hereinafter, "examination") performed by the MRI apparatus 100. The magnetic resonance imaging is an imaging method by which an atomic nucleus spin of the patient P placed in a static magnetic field is magnetically excited by a Radio Frequency (RF) pulse having a Larmor frequency thereof so as to generate an image from data of a magnetic resonance signal (hereinafter, "MR signal") occurring due to the excitation. For this reason, a strong magnetic field occurs from the MRI apparatus 100.

An imaging room R1 in which the MRI apparatus 100 is installed is a shield room configured so that no external electromagnetic waves are allowed to enter the imaging room R1 and so that all the electromagnetic waves occurring from the MRI apparatus 100 are confined in the imaging room R1 and prevented from leaking to the outside. A door 500 at the entrance of the imaging room R1 is connected to a control room R2. The patient P and users such as a technologist 1 enter the imaging room R1 through the door 500. The door 500 also serves as an exit from the imaging room R1. The user such as the technologist 1 is an example of a medical worker. The user (e.g., the technologist 1) in the present embodiment may be replaced by another medical worker such as a medical doctor, a nurse, or the like. The user does not necessarily have to be a medical worker. In the following sections, an example will be explained in which the user is the technologist 1.

The positional relationship between the imaging room R1 and the control room R2 is not limited to the example illustrated in FIG. 1. For instance, the imaging room R1 may be provided with one or more other entrances and/or exits leading to another room besides the control room R2 and/or a hallway. In the control room R2, a console device 300 connected to the MRI apparatus 100 is installed.

The console device 300 is used for managing the MRI apparatus 100. For example, the console device 300 is configured to display the magnetic resonance image taken by the MRI apparatus 100. Further, the console device 300 is configured to transmit information such as an image taking condition (an imaging condition) of the MRI apparatus 100 input by the user, to the MRI apparatus 100. For example, the console device 300 may be a personal Computer (PC) including a storage circuitry, a processing circuitry such as a Central Processing Unit (CPU), a network (NW) interface, an input interface, a display device, and the like. The console device 300 may be realized by a computer system 130 included in the MRI apparatus 100.

For example, the tablet terminal 200 includes a storage circuitry, a processing circuitry such as a CPU, a NW interface, an input interface, a display device, a camera, and the like. The input interface of the tablet terminal 200 is a touch screen in which a display device and a touchpad are integrally formed. For example, the tablet terminal 200 is used by the technologist 1 to interview the patient P, before the patient P undergoes the examination performed by the MRI apparatus 100. For example, to the tablet terminal 200, the technologist 1 who operates the MRI apparatus 100 inputs various types of information, by interviewing the patient P to be examined by the MRI apparatus 100. The tablet terminal 200 has a wireless communication function and is connected to the computer system 130 included in the MRI apparatus 100 while communication therebetween is enabled. Further, the tablet terminal 200 may also be communicably connected to an information processing system in the medical institution such as a Hospital Information System (HIS) or a Radiology Information System (RIS).

In the following sections, to explain a specific example, information (hereinafter, "interview data") input as a result of interviewing the patient P and data (hereinafter, "identification data") for identifying the patient P at the time of the inputs at the interview will collectively be referred to as input relevant information. The information that may be input at the interview includes, for example, subjective symptoms at present, a medical history, medications being taken, a family history, an allergy history, and a travel history of the patient P. The identification data includes patient information such as a patient ID of the patient P, an examination ID, the name of the patient P, the date of birth of the patient P, the weight and the height of the patient P, symptoms of the patient P, and the like.

At the interview, the technologist 1 checks the identity of the patient P, explains things to keep in mind regarding the imaging process to be performed by the MRI apparatus 100, and the like. After interviewing the patient P, the technologist 1 guides the patient P to the imaging room R1 and enters the imaging room R1 together with the patient P. After that, the technologist 1 places the patient P on a couchtop 105a of a couch 105 of the MRI apparatus 100, stabilizes the posture of the patient P, and sets a radio frequency (RF) coil.

Figure 3:
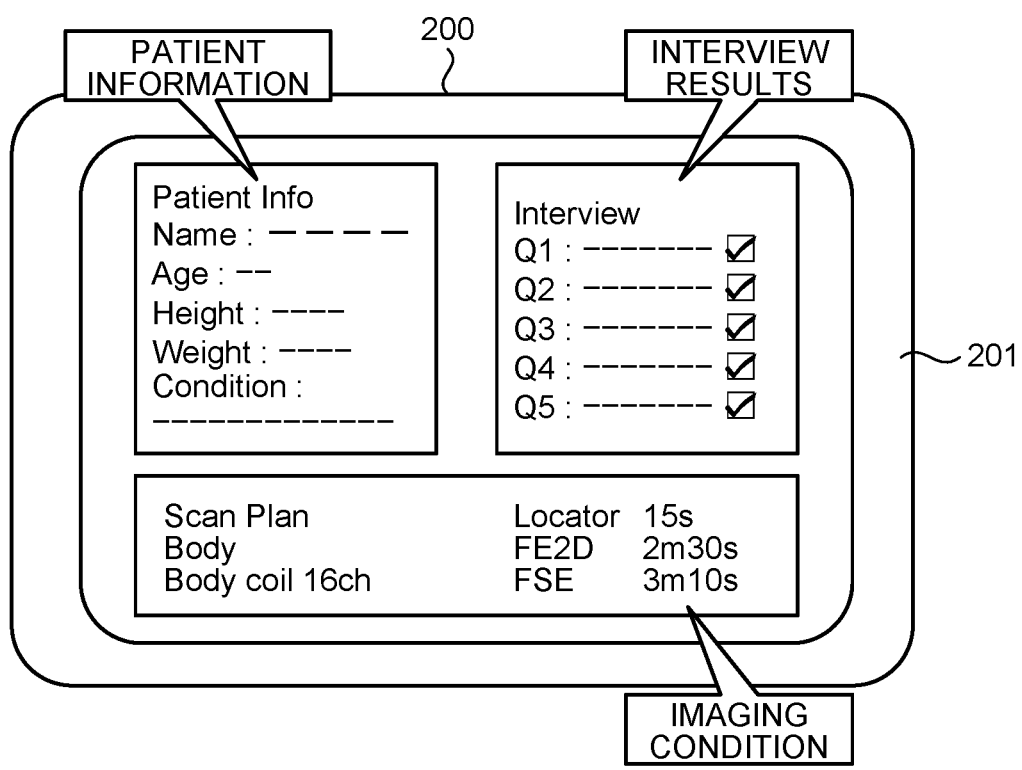
FIG. 3 is a drawing illustrating an example of an interview screen displayed on a tablet terminal according to the first embodiment.

FIG. 3 is a drawing illustrating an example of an interview screen displayed on the tablet terminal 200 according to the first embodiment. As illustrated in FIG. 3, a display device 201 of the tablet terminal 200 displays the input relevant information. In other words, the display device 201 of the tablet terminal 200 displays: the patient information of the patient P corresponding to the identification data; interview results corresponding to the interview data; and the image taking condition used in the MRI process performed on the patient P. The patient information and the image taking condition are, for example, obtained by the tablet terminal 200 from the HIS, the RIS, or the MRI apparatus 100 and displayed by the display device 201. Alternatively, the patient information and the image taking condition may be input by the technologist 1 via the tablet terminal 200. Also, the technologist 1 inputs information provided by the patient P at the time of interviewing the patient P, to the tablet terminal 200 as the interview results.

For example, in the imaging room R1, the mount unit 510 capable of having the tablet terminal 200 mounted thereon is provided in the vicinity of the couch 105. Being "mounted thereon" is not limited to simply being "placed thereon" and may denote being "held" or the like. In an example, the mount unit 510 may be realized as a mount base capable of having the tablet terminal 200 mounted thereon or a tablet holder capable of holding the tablet terminal 200. In the following sections, to explain a specific example, the mount unit 510 is assumed to be a mount base. The mount base 510 does not necessarily have to be a stand-alone device such as that illustrated in FIG. 1 and may be installed, for example, as a tablet holder in the vicinity of a handle 105b provided at an end part of the couchtop 105a of the couch 105. As illustrated in FIG. 1, with respect to a gantry 10, the handle 105b is positioned apart from the gantry 10. For this reason, the tablet terminal 200 mounted on the tablet holder in the vicinity of the handle 105b does not necessarily need to have an anti-magnetic function (a magnetic shield).

The mount base 510 is capable of having the tablet terminal 200 mounted thereon. The mount base 510 includes a mechanism configured to hold the mounted tablet terminal 200. For example, the mount base 510 includes a connector, a detecting unit 511, and a transmitting unit 513. The connector is electrically connected to the tablet terminal 200 mounted on the mount base 510. The connector is provided in such a position on the mount base 510 that, when the tablet terminal 200 is installed on the mount base 510, the connector is connected to an input/output terminal of the tablet terminal 200.

The detecting unit 511 is configured to detect whether or not the tablet terminal 200 is mounted on the mount base 510. For example, when the tablet terminal 200 is installed on the mount base 510, the detecting unit 511 detects that the tablet terminal 200 is installed on the mount base 510 (hereinafter, "terminal mount"), on the basis of an electric current flow to the tablet terminal 200 via the connector. The detecting unit 511 is realized by using a detecting circuitry configured to detect the terminal mount. In this situation, the detecting unit 511 does not necessarily have to be a detecting circuitry and may be realized by using any of various types of sensors. For example, the detecting unit 511 may be realized by using a sensor which is provided in a prescribed region of the mount base 510 having the tablet terminal 200 mounted thereon and of which a switch is turned on as a result of the tablet terminal 200 being mounted. The sensor may be a sensor turned on when being mechanically pressed or may be a contact sensor configured to detect contact with the tablet terminal 200. The method used by the sensor to detect the tablet terminal 200 is not particularly limited.

The transmitting unit 513 is configured to transmit any of the data stored in the tablet terminal 200 connected to the connector, to the MRI apparatus 100. For example, the transmitting unit 513 is realized by using a transmission circuitry related to data transmission. For example, when the detecting unit 511 detects that the tablet terminal 200 is mounted on the mount base 510, the transmitting unit 513 transmits the input relevant information from the tablet terminal 200 to the MRI apparatus 100. In this situation, of the input relevant information, the transmitting unit 513 may transmit the identification data that makes it possible to identify the patient P, to the MRI apparatus 100. More specifically, as being triggered by the detection of the terminal mount, the transmitting unit 513 transmits a signal (hereinafter, "detection signal") indicating the terminal mount and the identification data, to the computer system 130 included in the MRI apparatus 100. The transmission from the transmitting unit 513 to the computer system 130 is realized in a wired or wireless manner. Alternatively, the detecting unit 511 and the transmitting unit 513 may be installed in the tablet terminal 200. In that situation, as being triggered by the detection of the terminal mount, the tablet terminal 200 transmits, by employing the transmitting unit 513, the detection signal and the identification data, to the computer system 130.

In another example, the mount base 510 does not necessarily need to include the connector, the detecting unit 511, and the transmitting unit 513. In that situation, a monitoring device configured to monitor whether the tablet terminal 200 is mounted on the mount base 510 is provided on a wall surface of the imaging room R1 or on the surface of the gantry 10, for example. For instance, the monitoring device includes an optical device capable of imaging the mount base 510 and the transmitting unit 513. The optical device included in the monitoring device may be, for example, an optical camera, a distance meter such as an electro-optical distance measuring instrument, or a Light Detection and Ranging (LIDAR) device. In the following sections, to explain a specific example, the optical device is assumed to be a camera. In that situation, the monitoring device successively is configured to generate images by imaging the mount base 510. The monitoring device is configured to determine whether or not the tablet terminal 200 is mounted on the mount base 510, on the basis of the taken images. In this situation, the monitoring device functions as the detecting unit 511 configured to detect the terminal mount. Because it is possible to determine whether the terminal mount has occurred or not by performing a known image processing process such as semantic segmentation, the explanations thereof will be omitted.

As being triggered by the detection of the terminal mount, the transmitting unit 513 included in the monitoring device is configured to transmit a detection signal to the computer system 130. For example, as being triggered by the detection of the terminal mount, the transmitting unit 513 included in the monitoring device establishes communication with the tablet terminal 200 and transmits the interview data and/or the identification data from the tablet terminal 200 to the computer system 130.

Next, a hardware configuration and functions of the MRI apparatus 100 according to the present embodiment will be explained. As illustrated in FIG. 2, the MRI apparatus 100 and the tablet terminal 200 are connected together by a network N1 such as an in-hospital Local Area Network (LAN). In this situation, the tablet terminal 200 may be connected to the MRI apparatus 100 by the network N1 via the connector and the monitoring device included in the mount base 510. The method for connecting the devices is not limited to wireless communication and may be realized by wired communication or a connection using a dedicated cable different from the network N1.

Further, the network N1 may further be connected to the HIS or the RIS including an electronic medical record system or to any of various types of server devices and the like installed in the medical institution in which the imaging room R1 is provided.

As illustrated in FIG. 2, the MRI apparatus 100 includes the gantry 10, the couch 105, and the computer system 130. The gantry 10 includes an imaging system related to the imaging of the patient P examined by the MRI apparatus 100. More specifically, the gantry 10 includes a static magnetic field magnet 101, a static magnetic field power source (not illustrated), a gradient coil 103, a gradient power source 104, a couch controlling circuitry 106 configured to control the couch 105, a transmission coil 107, a transmission circuitry 108, a reception coil 109, a reception circuitry 110, a sequence controlling circuitry 120, and a monitor 136.

The configuration illustrated in FIG. 2 is merely an example. For instance, any of the functional units of the sequence controlling circuitry 120 and the computer system 130 may be integrated together or separated from the others, as appropriate. Further, at least one selected from among the static magnetic field power source (not illustrated), the gradient power source 104, the couch controlling circuitry 106, the transmission circuitry 108, and the reception circuitry 110 may be arranged in the imaging room R1 and/or the control room R2, instead of being installed in the gantry 10. The patient P is not included in MRI apparatus 100.

The static magnetic field magnet 101 is a magnet formed to have a hollow and substantially circular cylindrical shape and is configured to generate the static magnetic field in the space on the inside thereof. For example, the static magnetic field magnet 101 is a superconductive magnet, a permanent magnet, or the like. When the static magnetic field magnet 101 is a permanent magnet, the MRI apparatus 100 does not necessarily have to include the static magnetic field power source. Further, the static magnetic field power source may be provided separately from the MRI apparatus 100.

The gradient coil 103 is a coil formed to have a hollow and substantially circular cylindrical shape and is arranged on the inside of the static magnetic field magnet 101. The gradient coil 103 is configured to generate gradient magnetic fields of which the magnetic field intensities change along X-, Y-, and Z-axes that are orthogonal to one another. Further, under control of the sequence controlling circuitry 120, the gradient power source 104 is configured to supply electric currents to the gradient coil 103.

The couch 105 includes the couchtop 105a on which the patient P is placed. Further, the couch 105 includes a driving function structured with: an actuator using any of various types of motors to drive the couchtop 105a and the couch 105; and a motive power transmission unit configured to transmit motive power generated by the actuator to movable parts. As for the couch 105, under the control of the couch controlling circuitry 106 exercised on the driving function, the couchtop 105a is inserted into an imaging opening 137, while the patient P is placed thereon. Under control of the computer system 130, the couch controlling circuitry 106 is configured to drive the couch 105 so as to move the couchtop 105a in longitudinal directions and up-and-down directions.

The transmission coil 107 is configured to generate a radio frequency magnetic field by receiving a supply of the RF pulse from the transmission circuitry 108 and to apply the radio frequency magnetic field to the patient P. Under control of the sequence controlling circuitry 120, the transmission circuitry 108 is configured to supply the RF pulse to the transmission coil 107.

The reception coil 109 is arranged on the inside of the gradient coil 103 and is configured to receive the MR signal emitted from the patient P due to influence of the radio frequency magnetic field. The reception coil 109 is configured to output the received MR signal to the reception circuitry 110. It is also acceptable to use a configuration in which the reception coil 109 serves also as the transmission coil 107.

The reception circuitry 110 is configured to generate MR data by performing an Analog/Digital (A/D) conversion on the MR signal which is analog and is output from the reception coil 109. The reception circuitry 110 is configured to transmit the generated MR data to the sequence controlling circuitry 120. Alternatively, the A/D conversion may be performed in the reception coil 109. Further, besides the A/D conversion, the reception circuitry 110 is capable of performing other arbitrary signal processing processes.

The sequence controlling circuitry 120 is configured to perform the imaging process on the patient P, by driving the gradient power source 104, the transmission circuitry 108, and the reception circuitry 110 on the basis of sequence information transmitted thereto from the computer system 130. The sequence information is information defining a procedure for performing the imaging process. The sequence controlling circuitry 120 may be realized by using a processor or may be realized by using a combination of software and hardware. Further, when having received the MR data from the reception circuitry 110 as a result of imaging the patient P by driving the gradient power source 104, the transmission circuitry 108, and the reception circuitry 110, the sequence controlling circuitry 120 is configured to transfer the received MR data to the computer system 130.

The computer system 130 is configured to control the entirety of the MRI apparatus 100, to generate the MR image, and the like. As illustrated in FIG. 2, the computer system 130 includes a NW interface 131, a storage circuitry 132, a processing circuitry 133, an input interface 134, a display device 135, and the like.

The storage circuitry 132 is configured to store therein the MR data received by the NW interface 131, k-space data arranged in a k-space by the processing circuitry 133 (explained later), image data generated by the processing circuitry 133, and the like. For example, the storage circuitry 132 is realized by using a semiconductor memory element such as a Random Access Memory (RAM) or a flash memory, or a hard disk, an optical disk, or the like.

The input interface 134 is configured to receive various types of instructions and inputs of information from an operator. For example, the input interface 134 is realized by using a trackball, a switch button, a mouse, a keyboard, a touchpad on which an input operation can be performed by touching an operation surface thereof, a touch screen in which a display screen and a touchpad are integrally formed, a contactless input circuitry using an optical sensor, an audio input circuitry, and/or the like. The input interface 134 is connected to the processing circuitry 133 and is configured to convert the input operations received from the operator into electrical signals and to output the electrical signals to the processing circuitry 133. In the present disclosure, the input interface 134 does not necessarily have to include one or more physical operational component parts such as a mouse, a keyboard, and/or the like. Examples of the input interface 134 include, for instance, an electrical signal processing circuitry configured to receive electrical signals corresponding to the input operations from an external input device provided separately from the computer system 130 and to output the electrical signals to a controlling circuitry.

Under control of the processing circuitry 133, the display device 135 is configured to display various types of Graphical User Interfaces (GUIs), a guidance screen for the technologist 1, a magnetic resonance image generated by the processing circuitry 133, or the like. For example, the display device 135 is a displaying device such as a liquid crystal display device.

For example, the monitor 136 is positioned so as to be visually recognizable by the technologist 1 operating the MRI apparatus 100 and the patient P examined by the MRI apparatus 100. For example, the monitor 136 is realized by using a displaying device such as a liquid crystal display device. The monitor 136 is provided in the imaging room R1. Being positioned so as to be visually recognizable by the technologist 1 and the patient P denotes, for example, being positioned straight above the imaging opening 137 (which may simply be called "opening") on the counterface of the gantry 10 facing the couch 105, as illustrated in FIG. 1. In an example, it is acceptable to provide, on at least one of the left and the right ends from the position where the monitor 136 is installed, a holder (hereinafter, "gantry front-face holder") capable of holding the tablet terminal 200 equipped with an anti-magnetic function. In that situation, the gantry front-face holder corresponds to the mount base 510 and may have the various types of units and the various types of functions of the mount base 510 described above.

The processing circuitry 133 is configured to control the entirety of the MRI apparatus 100. More specifically, in an example, the processing circuitry 133 includes an imaging processing function 133a, a matching function 133b, and a controlling function 133c. The imaging processing function 133a is an example of an imaging processing unit. The matching function 133b is an example of a matching unit. A controlling function 133c is an example of the controlling unit.

The abovementioned detecting unit 511 may be realized as the detecting function of the processing circuitry 133. In that situation, the detecting function is configured to detect the terminal mount on the basis of an electric current flow to the tablet terminal 200 via the connector. Further, upon receipt of an output from the sensor installed on the mount base 510, the detecting function is configured to detect the terminal mount. Alternatively, on the basis of an image output from the optical device included in the monitoring device and various types of information such as distance data, the detecting function is configured to detect the terminal mount.

The processing functions of the constituent elements of the processing circuitry 133, namely, the imaging processing function 133a, the matching function 133b, and the controlling function 133c, are stored in the storage circuitry 132 in the form of computer-executable programs. The processing circuitry 133 is a processor. For example, the processing circuitry 133 is configured to realize the functions corresponding to the programs by reading and executing the programs from the storage circuitry 132. In other words, the processing circuitry 133 that has read the programs has the functions illustrated within the processing circuitry 133 in FIG. 2. Although the example was explained with reference to FIG. 2 in which the single processor realizes the processing functions executed by the imaging processing function 133a, the matching function 133b, and the controlling function 133c, it is also acceptable to structure the processing circuitry 133 by combining together a plurality of independent processors, so that the functions are realized as a result of the processors executing the programs. Further, although the example was explained with reference to FIG. 2 in which the single storage circuit (i.e., the storage circuitry 132) has stored therein the programs corresponding to the processing functions, it is also acceptable to provide a plurality of storage circuits in a distributed manner, so that the processing circuitry 133 reads a corresponding program from each of the individual storage circuits.

The imaging processing function 133a is configured to carry out the imaging process to take the magnetic resonance image by controlling functional units of the MRI apparatus 100. More specifically, the imaging processing function 133a is configured to generate the sequence information, to acquire the MR data, to generate the k-space data, and to generate the magnetic resonance image. The imaging processing function 133a is configured to save the generated magnetic resonance image into the storage circuitry 132, for example.

The matching function 133b is configured to match appointment list data representing an appointment list of examinations performed by the MRI apparatus 100 against the identification data. More specifically, upon receipt of the detection signal from the transmitting unit 513, the matching function 133b reads the appointment list data transmitted from the RIS, from the storage circuitry 132. The matching function 133b identifies data (hereinafter, "examination appointment data") representing an examination appointment being closest in time within the appointment list data.

The examination appointment data is, for example, related to an examination order transmitted from the HIS to the RIS and includes an examination ID, a patient ID, an examination date/time, and the like. The matching function 133b matches the identified examination appointment data against the identification data transmitted from the transmitting unit 513. The matching function 133b judges whether or not the examination IDs, the patient IDs, and the like match between the examination appointment data being closest in time (hereinafter, "closest examination appointment data") and the identification data.

For example, when the patient IDs match between the closest examination appointment data and the identification data, the matching function 133b is configured to output, to the controlling function 133c, information (hereinafter, "match information") related to the match between the closest examination appointment data and the identification data. On the contrary, when neither the examination IDs nor the patient IDs match between the closest examination appointment data and the identification data, the matching function 133b is configured to output, to the controlling function 133c, information (hereinafter, "non-match information") related to the non-match between the closest examination appointment data and the identification data.

When it is detected that the tablet terminal 200 is mounted on the mount base 510, the controlling function 133c is configured to exercise various types of control over the MRI apparatus 100. For example, upon receipt of the detection signal from the transmitting unit 513, the controlling function 133c is configured to cause a display device such as the monitor 136 to display the input relevant information related to the patient P. In this situation, when the closest examination appointment data matches the identification data, i.e., as being triggered by receipt of the match information, the controlling function 133c may cause the monitor 136 to display the input relevant information. The display of the input relevant information on the monitor 136 is display of, for example, the patient information such as the patient ID, the examination ID, the name of the patient P, the date of birth of the patient P, the weight and the height of the patient P, and/or the like. The controlling function 133c may cause the monitor 136 to display the interview data.

When the closest examination appointment data does not match the identification data, i.e., as being triggered by receipt of the non-match information, the controlling function 133c is configured to cause the monitor 136 to display an instruction to check the input relevant information. The instruction to check the input relevant information is, for example, a character string to prompt the technologist 1 to check to see whether or not the patient P related to the closest examination appointment data is the same as the patient P who took the interview. The instruction corresponds to checking the identity of the patient P. The instruction to check the input relevant information is presented as a check dialogue box, for example. The check dialogue box may display, for example, a character string "Is this OK?" to ask for an approval on the display of the input relevant information related to the patient P who took the interview and a push button "OK" representing an input of the approval in response to the character string.

When the approval is input in response to the instruction to check the input relevant information, the controlling function 133c is configured to cause the monitor 136 to display the input relevant information related to the patient P who took the interview. The input of the approval in response to the instruction to check the input relevant information is, for example, realized by pressing the "OK"

button in the check dialogue box displayed on the monitor 136 as being triggered by the receipt of the non-match information. In this situation, as being triggered by the receipt of the non-match information, the controlling function 133c may change the sequential order of the examinations in the appointment list so as to prioritize the examination of the patient P and further cause the monitor 136 to display the input relevant information related to the patient P.

In the explanations above, the example was explained in which the "processor" reads and executes the programs corresponding to the functions, from the storage circuitry 132; however, possible embodiments are not limited to this example. The term "processor" denotes, for example, a CPU, a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]).

When the processor is a CPU, for example, the processor realizes the functions by reading and executing the programs saved in the storage circuitry 132. Alternatively, when the processor is an ASIC, the functions are directly incorporated, as a logic circuitry, into the circuitry of the processor, instead of the programs being saved in the storage circuitry 132. The processors according to the present embodiment do not each necessarily have to be structured as a single circuit. It is also acceptable to structure one processor by combining together a plurality of independent circuits, so as to realize the functions thereof. Further, two or more of the constituent elements illustrated in FIG. 2 may be integrated into a single processor so as to realize the functions thereof.

Figure 4:
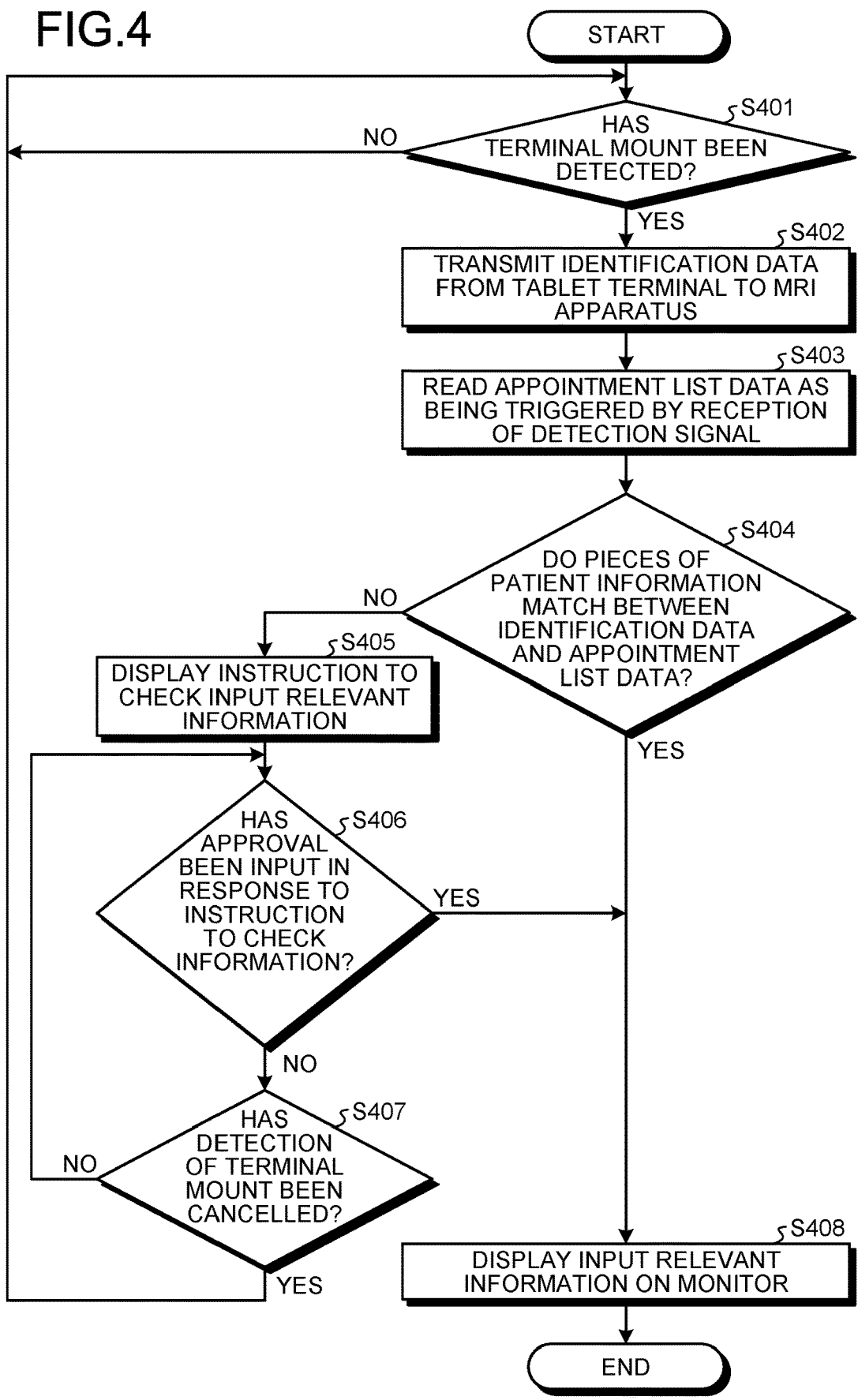
FIG. 4 is a flowchart illustrating an example of a flow in a display controlling process according to the first embodiment.

Next, a process (hereinafter, "display controlling process") to control the display of the MRI apparatus 100 performed by the medical image diagnosis system S1 according to the present embodiment structured as described above will be explained, with reference to FIG. 4. FIG. 4 is a flowchart illustrating an example of a flow in the display controlling process according to the first embodiment. The display controlling process:

At a stage preceding the process in FIG. 4, the results of the interview with the patient P are input to the tablet terminal 200 by the technologist 1. After that, while carrying the tablet terminal 200, the technologist 1 moves from the outside of the imaging room R1 to the inside of the imaging room R1, together with the patient P.

Step S401:

It is judged whether or not the terminal mount has been detected. More specifically, when the tablet terminal 200 is mounted on the mount base 510, the detecting unit 511 detects the terminal mount (step S401: Yes). In this situation, the process at step S402 will be performed. On the contrary, when no terminal mount is detected by the detecting unit 511 (step S401: No), for example, unless the tablet terminal 200 is mounted on the mount base 510, the process at step S401 is repeatedly performed.

Step S402:

The identification data is transmitted from the tablet terminal 200 to the MRI apparatus 100. More specifically, the transmitting unit 513 transmits the input relevant information from the tablet terminal 200 to the MRI apparatus 100. More specifically, of the input relevant information, the transmitting unit 513 transmits the identification data that makes it possible to identify the patient P, to the MRI apparatus 100.

Step S403:

As being triggered by receipt of the detection signal, the closest examination appointment data in the appointment list data is identified. More specifically, upon the receipt of the detection signal transmitted from the transmitting unit 513, the matching function 133b reads the appointment list data transmitted from the RIS, from the storage circuitry 132. Subsequently, the matching function 133b identifies the closest examination appointment data in the appointment list data.

Step S404:

It is judged whether the pieces of patient information match or do not match, between the identification data and the examination appointment data. More specifically, the matching function 133b matches the identified examination appointment data against the identification data transmitted from the transmitting unit 513. The matching function 133b judges whether or not the pieces of patient information (e.g., the examination IDs, the patient IDs) match between the closest examination appointment data and the identification data. When the pieces of patient information match between the closest examination appointment data and the identification data (step S404: Yes), the matching function 133b outputs match information to the controlling function 133c. In this situation, the process at step S408 will be performed. On the contrary, when the pieces of patient information do not match between the closest examination appointment data and the identification data (step S404: No), the matching function 133b outputs non-match information to the controlling function 133c. In this situation, the process at step S405 will be performed.

Step S405:

The monitor 136 displays the instruction to check the input relevant information. More specifically, as being triggered by receipt of the non-match information, the controlling function 133c causes the monitor 136 to display the check dialogue box. The process at the present step corresponds to checking the identity of the patient P related to the examination.

Step S406:

It is judged whether or not an approval is input in response to the instruction to check the input relevant information. More specifically, when pressing of the "OK" button in the check dialogue box is input by the input interface 134 or the tablet terminal 200 (step S406: Yes), the process at step S408 will be performed. In this situation, the controlling function 133c changes the sequential order of the examinations in the appointment list so as to prioritize the examination of the patient P. In addition, the controlling function 133c transmits the changed appointment list to the RIS via the NW interface 131. Accordingly, the appointment list in the RIS is updated with the examination list prioritizing the examination of the patient P. On the contrary, when pressing of the "OK" button in the check dialogue box is not input by the input interface 134 or the tablet terminal 200 (step S406: No), the process at step S407 will be performed.

Step S407:

It is judged whether or not the detection of the terminal mount has been cancelled. More specifically, when the tablet terminal 200 is released from the mount base 510 (step S407: Yes), the process at step S401 will be performed. In this situation, until the tablet terminal 200 is mounted on the mount base 510, the process at step S401 will be repeatedly performed. On the contrary, when the tablet terminal 200 has not been released from the mount base 510 (step S407: No), the process at step S406 will be performed.

Step S408:

The monitor 136 displays the input relevant information. More specifically, the controlling function 133c causes the monitor 136 to display the input relevant information. For example, the controlling function 133c causes the monitor 136 to display the patient information. As a result, it is possible to cause the monitor 136 to display the input relevant information related to the patient P, while avoiding the situation where the patient P is able to visually recognize personal information of other patients besides the patient P. The display controlling process ends at the present step. After that, the imaging process will be performed on the patient P. While the MRI apparatus 100 is in operation, the display controlling process will be repeatedly performed. In that situation, when the tablet terminal 200 is mounted on the mount base 510, the processes at step S408 and thereafter will be performed.

In a modification example of the technical concepts of the present embodiment, for example, steps S402 through S407 in the display controlling process in FIG. 4 may be omitted. In that situation, as being triggered by the receipt of the detection signal, the controlling function 133c causes the monitor 136 to display the input relevant information. In this configuration, because the matching between the closest examination appointment data and the identification data is not performed, the matching function 133b is not included in the processing circuitry 133. Further, the judgment related to displaying the input relevant information on the monitor 136 is not limited to the example described above and may be arbitrarily modified by setting a security level of the information disclosure as appropriate.

Further, in a yet another modification example of the technical concepts of the present embodiment, in addition to omitting steps S402 through S407, the transmission of the input relevant information from the tablet terminal 200 to the MRI apparatus 100 may also be omitted, for example. In that situation, as being triggered by the receipt of the detection signal from the detecting unit 511, the controlling function 133c is configured to cause the monitor 136 to display the patient information and the like in the closest examination appointment data stored in the storage circuitry 132. In that situation, the transmitting unit 513 and the matching function 133b may be omitted.

In an application example of the technical concepts of the present embodiment, it is possible to apply, as appropriate, the display controlling process illustrated in FIG. 4 to another modality such as an X-ray CT apparatus, an X-ray diagnosis apparatus, a nuclear medicine diagnosis apparatus, or an ultrasound diagnosis apparatus.

In the medical image diagnosis system S1 according to the first embodiment described above, it is detected whether or not the mobile terminal is mounted on the mount unit 510 capable of having the mobile terminal mounted thereon. When it is detected that the mobile terminal is mounted on the mount unit 510, the control is exercised over the medical image diagnosis apparatus. More specifically, in the medical image diagnosis system S1 described herein, while being visually recognizable by the technologist 1 operating the medical image diagnosis apparatus and the patient P examined by the medical image diagnosis apparatus, the monitor 136 is configured to display the input relevant information relevant to the input to the mobile terminal regarding the patient P. Accordingly, when the medical image diagnosis system S1 described herein is used, the monitor 136 or the like is configured to display the interview data or the patient information related to the patient P, as being triggered by the mounting of the mobile terminal carried around by the technologist 1 on the mount unit 510. Consequently, it is possible to improve work efficiency of the technologist 1 in assisting the patient P prior to the imaging process such as providing guidance at the time of placing the patient P on the couch 105 and in various types of checking procedures performed by the technologist 1 for the patient P.

Further, in the medical image diagnosis system S1 according to the first embodiment described herein, when it is detected that the mobile terminal is mounted on the mount unit 510, the identification data that is included in the input relevant information and makes it possible to identify the patient P is transmitted from the mobile terminal to the medical image diagnosis apparatus, so that the appointment list data representing the appointment list of the examinations performed by the medical image diagnosis apparatus is matched against the identification data. When the closest examination appointment data in the appointment list data matches the identification data, the monitor 136 is configured to display the input relevant information. When the closest examination appointment data does not match the identification data, the monitor 136 is configured to display the instruction to check the input relevant information. Accordingly, when the medical image diagnosis system S1 described herein is used, the process of checking the identity of the patient P related to the examination is performed, as being triggered by the mounting of the mobile terminal carried around by the technologist 1 on the mount unit 510. It is therefore possible to improve work efficiency of the technologist 1, in the various types of checking procedures for the patient P.

Further, when the medical image diagnosis system S1 according to the first embodiment described herein is used, when the closest examination appointment data and the identification data do not match, the sequential order of the examinations in the appointment list is changed so as to prioritize the examination of the patient P, and the monitor 136 is configured to display the input relevant information. Accordingly, when the medical image diagnosis system S1 described herein is used, as being triggered by the mounting of the mobile terminal carried around by the technologist 1 on the mount unit 510, it is possible to perform the examination of the patient P with priority, even when the closest examination appointment data and the identification data do not match, and is also possible to automatically change the sequential order of the examinations in the appointment list. It is therefore possible to improve work efficiency of the technologist 1 in the various types of checking procedures for the patient P.

Second Embodiment

Figure 5:
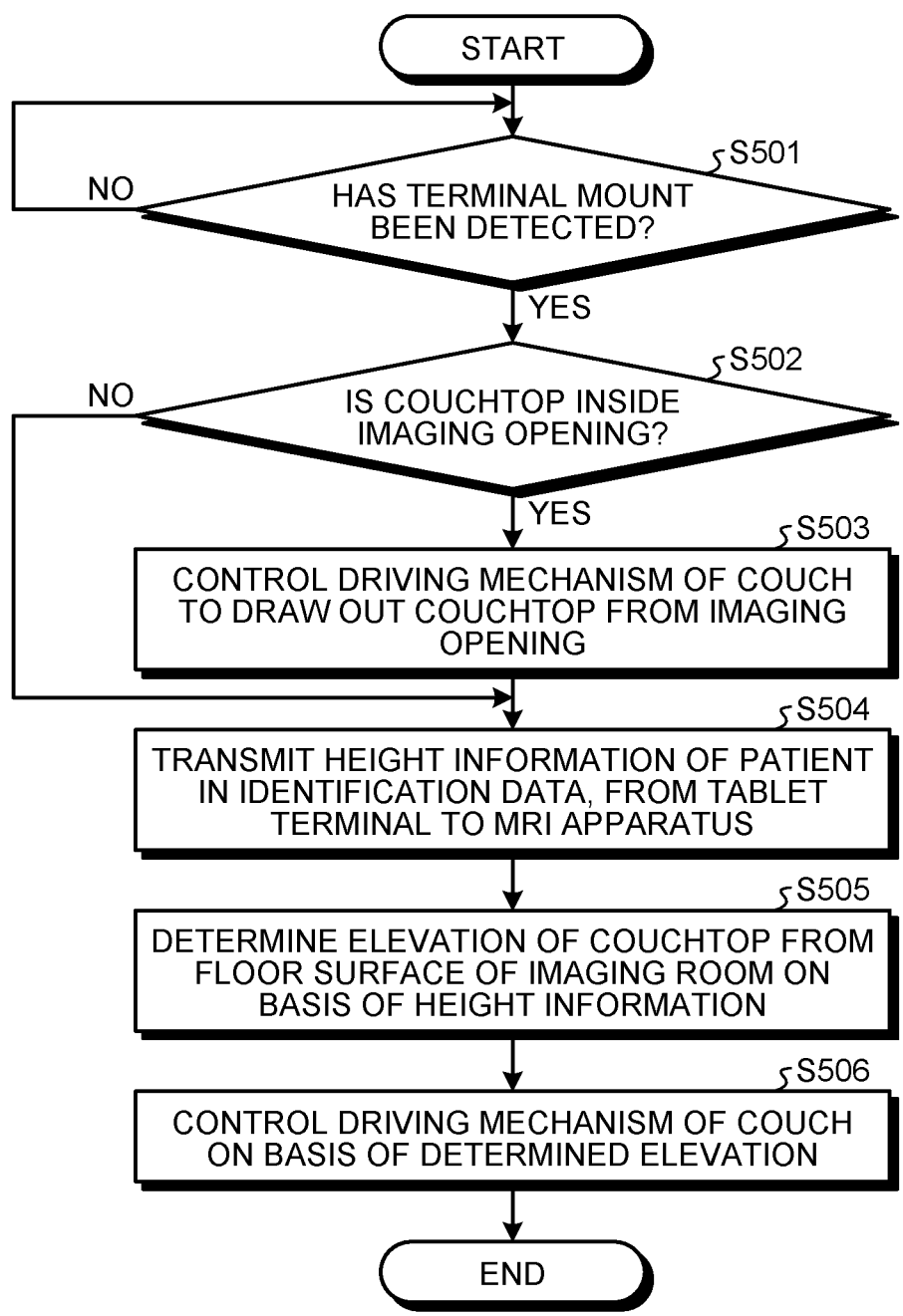
FIG. 5 is a flowchart illustrating an example of a flow in a drive controlling process according to a second embodiment.

In a second embodiment, as being triggered by receipt of the detection signal, the controlling function 133c is configured to switch a controlled status of a movable part of the medical image diagnosis apparatus. For example, in the second embodiment, as being triggered by the receipt of the detection signal, a driving mechanism of a movable part included in the MRI apparatus 100 is controlled so as to change the state of the movable part. In this situation, the movable part may be the couch 105, for example. The state of the movable part denotes, for example, one or both of: the elevation of the couch 105; and the position of the couchtop 105a of the couch 105. For example, the controlling function 133c controls the driving mechanism on the basis of information about the height of the patient P (hereinafter, "height information") in the identification data. In the following sections, a process (hereinafter, "drive controlling process")

to control the driving of the MRI apparatus 100 performed by the medical image diagnosis system S1 according to the present embodiment will be explained with reference to FIG. 5. FIG. 5 is a flowchart illustrating an example of a flow in the drive controlling process according to the second embodiment.

The Drive Controlling Process:

Step S501:

It is judged whether or not the terminal mount has been detected. More specifically, when the tablet terminal 200 is mounted on the mount base 510, the detecting unit 511 detects the terminal mount (step S501: Yes). In this situation, the process at step S502 will be performed. Because the other aspects of the process are the same as at step S401, the explanations thereof will be omitted.

Step S502:

It is judged whether or not the couchtop 105a is arranged on the inside of the imaging opening 137, i.e., in the cylindrical opening of the gantry 10. More specifically, on the basis of the position of the couchtop 105a recognized by any of the various types of sensors provided for the couch 105 or the couch controlling circuitry 106, when the couchtop 105a is positioned inside the imaging opening 137 (step S502: Yes), the process at step S503 will be performed. On the contrary, when the couchtop 105a is not positioned inside the imaging opening 137 (step S502: No), the process at step S504 will be performed.

Step S503:

The driving mechanism of the couch 105 is controlled so as to draw out the couchtop 105a from the imaging opening 137. More specifically, the controlling function 133c controls the couch controlling circuitry 106 so as to draw out the couchtop 105a from the imaging opening 137. As a result, the couchtop 105a is drawn out from the imaging opening 137 to the outside of the gantry 10.

Step S504:

The height information of the patient P included in the identification data is transmitted from the tablet terminal 200 to the MRI apparatus 100. More specifically, the transmitting unit 513 transmits the height information of the patient P included in the identification data, from the tablet terminal 200 to the MRI apparatus 100. It is possible to perform the present step at any point in time after step S501 and before step S505. In other words, when it is detected that the tablet terminal 200 is mounted on the mount base 510, the transmitting unit 513 transmits the height information of the patient P examined by the MRI apparatus 100, from the tablet terminal 200 to the controlling function 133c.

Step S505:

On the basis of the height information, the elevation of the couchtop 105a from the floor surface of the imaging room R1 (hereinafter, the elevation of the couch 105) is determined. More specifically, the controlling function 133c determines the elevation of the couch 105 on which the patient P can easily be placed, in accordance with the height of the patient P indicated in the height information. The determined elevation is lower when the height of the patient P is shorter, whereas the determined elevation is higher when the height of the patient P is taller. The relationship between patients' heights and elevation levels of the couchtop 105a is stored in the storage circuitry 132 in advance in the form of a correspondence table, for example. The controlling function 133c determines the elevation of the couch 105, by matching the height information against the correspondence table read from the storage circuitry 132.

Step S506:

On the basis of the determined elevation, the controlling function 133c controls the driving mechanism of the couch 105. More specifically, the controlling function 133c outputs a control signal to the couch controlling circuitry 106, so that the top face of the couchtop 105a is positioned at the position corresponding to the determined elevation. According to the control signal, the couch controlling circuitry 106 controls the driving mechanism. Accordingly, the couchtop 105a is moved to the determined elevation level. The drive controlling process thus ends.

In a modification example of the technical concepts of the present embodiment, the couch 105 is a dockable couch capable of docking onto the gantry 10, while the state of the movable part denotes whether the power of the dockable couch is turned on or off. For example, when the terminal mount is detected at step S501, the power of the dockable couch is turned on. In other words, when the tablet terminal 200 is mounted on the mount unit 510 provided in the vicinity of the handle 105b of the dockable couch, the power of the dockable couch is turned on, so that the technologist 1 is able to operate the dockable couch. In that situation, casters on the dockable couch may be unlocked. Further, while the tablet terminal 200 is mounted (or held) on the mount unit 510 of the dockable couch, when the tablet terminal 200 enters a range defined with a predetermined distance from the gantry 10, the controlling function 133c or a controlling circuitry installed in the dockable couch may be configured, as a controlling unit, to control the driving mechanism of the movable part of the dockable couch so as to lock the casters of the dockable couch.

Further, in an application example of the technical concepts of the present embodiment, the processing target of the drive controlling process may be a couch provided for an X-ray CT apparatus, an X-ray diagnosis apparatus, or a nuclear medicine diagnosis apparatus. Further, when the medical image diagnosis apparatus included in the medical image diagnosis system S1 is an X-ray diagnosis apparatus, the movable part does not necessarily have to be the couch 105 and may be one of various types of movable mechanism devices (imaging systems) such as a C-arm or an Ω-arm. In that situation, the state of the movable part denotes whether or not a locked state related to moving of the imaging system is achieved. In that situation, as being triggered by the detection of the terminal mount, the mechanism device is unlocked, for example. Further, when the medical image diagnosis apparatus included in the medical image diagnosis system S1 is an ultrasound diagnosis apparatus, the movable part corresponding to the imaging system corresponds to an ultrasound probe, for example. In that situation, as being triggered by the detection of the terminal mount, the holding of the ultrasound probe held by the probe holder to hold the ultrasound probe is unlocked, for example. In another example, as being triggered by the detection of the terminal mount, casters related to moving of the ultrasound diagnosis apparatus may be unlocked.

In the medical image diagnosis system S1 according to the second embodiment described above, the driving mechanism of the movable part of the medical image diagnosis apparatus is controlled so as to change the state of the movable part. For example, when the movable part is the couch 105, the state of the movable part denotes one or both of: the elevation of the couch 105 and the position of the couchtop 105a of the couch 105. In another example, when the movable part is a dockable couch capable of docking onto the gantry 10, the state of the movable part denotes whether the power of the dockable couch is turned on or off. In yet another example, when the movable part is the imaging system related to the imaging of the patient P examined by the medical image diagnosis apparatus, the state of the movable part denotes whether or not the locked state related to the moving of the imaging system is achieved. Further, in the medical image diagnosis system S1 described herein, when it is detected that the mobile terminal is mounted on the mount unit 510, the driving mechanism is controlled on the basis of the height information of the patient P examined by the medical image diagnosis apparatus. With these arrangements, by using the medical image diagnosis system S1 described herein, it is possible to automatically control the movable part, upon detection that the mobile terminal is mounted on the mount unit 510. It is therefore possible to improve work efficiency of the technologist 1 in assisting the patient P prior to the imaging process.

Third Embodiment

In a third embodiment, preparation information related to preparing for the examination of the patient P is determined, on the basis of the interview data transmitted from the transmitting unit 513, so that the monitor 136 displays the determined preparation information.

Figure 6:
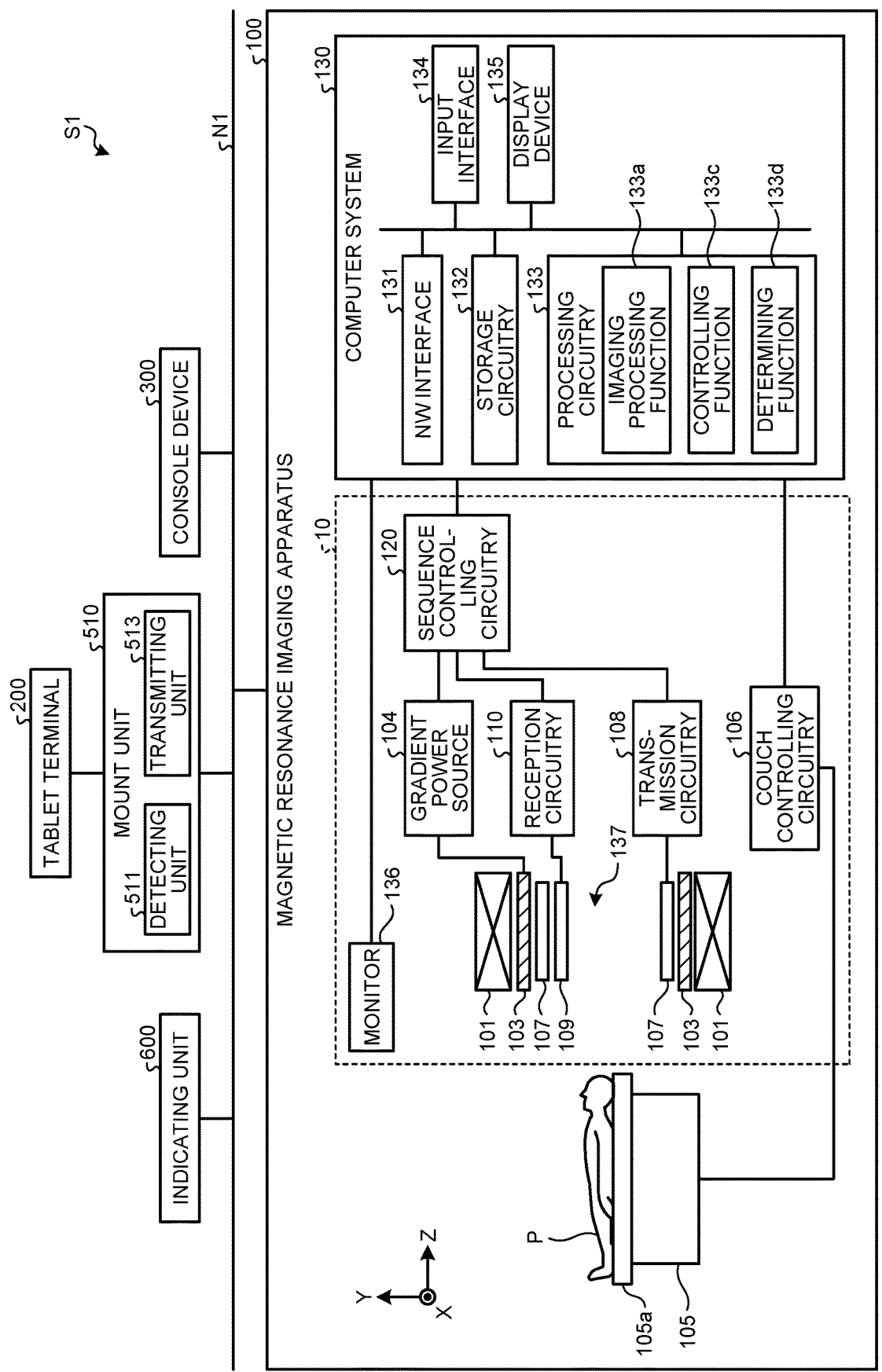
FIG. 6 is a block diagram illustrating an example of a medical image diagnosis system S1 including an MRI apparatus according to a third embodiment.

FIG. 6 is a block diagram illustrating an example of the medical image diagnosis system S1 including the MRI apparatus 100 according to the third embodiment. In an example, the processing circuitry 133 includes the imaging processing function 133*a*, the controlling function 133*c*, and a determining function 133*d*. The determining function 133*d* is an example of a determining unit.

To the tablet terminal 200, the technologist 1 inputs the interview data regarding the interview with the patient P related to the examination performed by the MRI apparatus 100. The interview data includes an imaging method related to the imaging process performed in the examination of the patient P. The imaging method may be output, in advance, from the MRI apparatus 100 to the tablet terminal 200 or may be input to the tablet terminal 200 by the technologist 1 in advance.

When it is detected that the tablet terminal 200 is mounted on the mount base 510, the transmitting unit 513 transmits the interview data from the tablet terminal 200 to the processing circuitry 133 related to the controlling function 133*c*.

The storage circuitry 132 stores therein a correspondence table indicating preparation information corresponding to contents of interview data and imaging methods. For example, the preparation information may be at least one of: the posture of the patient P during the examination, i.e., the posture of the patient P placed on the couchtop 105*a*; the type of the reception coil attached onto the patient P for the examination; and a procedure for attaching the reception coil onto the patient P. Examples of the posture of the patient P include a supine position, a lateral recumbent position, a prone position, a feet-first position where the patient is inserted into the imaging opening 137 with the feet entering first, and a head-first position where the patient is inserted into the imaging opening 137 with the head entering first.

The determining function 133*d* is configured to determine the preparation information related to the preparation for the examination of the patient P performed by the MRI apparatus 100, on the basis of the interview data transmitted from the tablet terminal 200 by the transmitting unit 513. For example, the determining function 133*d* determines the preparation information by using the contents of the interview in the interview data, the imaging method related to the examination of the patient P, and the correspondence table.

The controlling function 133*c* causes the preparation information to be displayed on the monitor 136 that is visually recognizable by the technologist 1 operating the MRI apparatus 100 and the patient P examined by the MRI apparatus 100. Further, via the network N1, the controlling function 133*c* may cause the display device 201 of the tablet terminal 200 to display, within the preparation information, work procedures such as a procedure for placing the patient P on the couchtop 105*a* and a procedure for attaching the reception coil onto the patient P. In this situation, the controlling function 133*c* may use the tablet terminal 200 mounted on the gantry front-face holder and the monitor 136 installed on the front face of the gantry 10 as a dual display system, so as to cause the preparation information to be displayed on the dual display system. In that situation, the controlling function 133*c* may cause the tablet terminal 200 and the monitor 136 to display a single piece of display content across the two screens.

On the basis of the preparation information, an indicating unit 600 is configured to indicate the location of the reception coil to be attached onto the patient P, from a coil storage shelf storing a plurality of reception coils. For example, the indicating unit 600 is realized by using a projector (e.g., a Light Emitting Device [LED]) capable of emitting light onto each of the plurality of reception coils stored on the coil storage shelf or an output device such as a speaker capable of outputting audio indicating the name of the reception coil to be attached onto the patient P.

Figure 7:
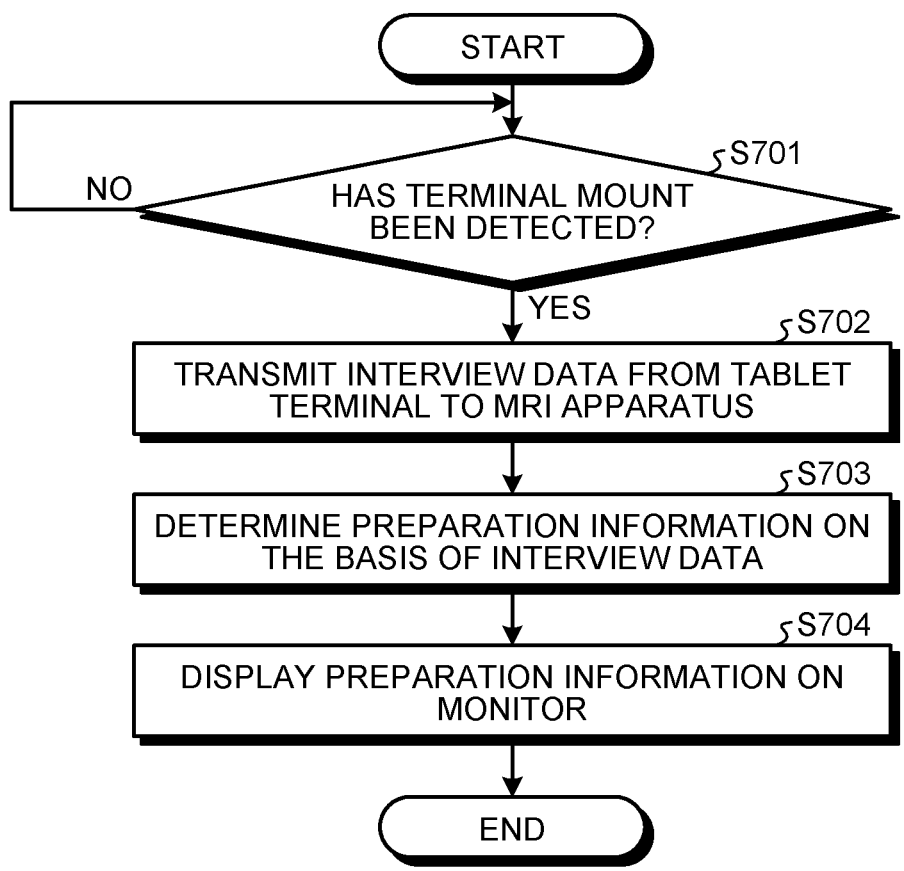
FIG. 7 is a flowchart illustrating an example of a flow in a preparation information display process according to the third embodiment.

Next, a process (hereinafter, "preparation information display process") to control the preparation information display of the MRI apparatus 100 performed by the medical image diagnosis system S1 according to the present embodiment will be explained, with reference to FIG. 7. FIG. 7 is a flowchart illustrating an example of a flow in the preparation information display process according to the third embodiment.

The preparation information display process:

Step S701:

It is judged whether or not the terminal mount has been detected. More specifically, when the tablet terminal 200 is mounted on the mount base 510, the detecting unit 511 detects the terminal mount (step S701: Yes). In this situation, the process at step S702 will be performed. Because the other aspects of the process are the same as at step S401, the explanations thereof will be omitted.

Step S702:

The interview data is transmitted from the tablet terminal 200 to the MRI apparatus 100. More specifically, the transmitting unit 513 transmits the interview data from the tablet terminal 200 to the MRI apparatus 100.

Step S703:

On the basis of the interview data, the preparation information is determined. More specifically, the determining function 133*d* determines the preparation information by using the interview data and the correspondence table.

Step S704:

The monitor 136 displays the preparation information. More specifically, the controlling function 133*c* causes the monitor 136 to display the determined preparation information. In this situation, on the basis of the preparation information, the indicating unit 600 indicates, from the coil storage shelf storing the plurality of reception coils, the location of the reception coil to be attached onto the patient P, by using audio or the LED. The indicating unit 600 may be omitted from the present embodiment. With the present step, the preparation information display process ends.

Further, in a modification example of the technical concepts of the present embodiment, it is possible to apply, as appropriate, the preparation information display process illustrated in FIG. 7 to another modality such as an X-ray CT apparatus, an X-ray diagnosis apparatus, or a nuclear medicine diagnosis apparatus. In this situation, the monitor 136 of any of these medical image diagnosis apparatuses and/or the display device 201 of the tablet terminal 200 are configured to display, as the preparation information, the posture of the patient P placed on the couchtop, for example. In that situation, the indicating unit 600 may output audio indicating the posture of the patient P placed on the couchtop.

In the medical image diagnosis system S1 according to the third embodiment described above, when it is detected that the mobile terminal is mounted on the mount unit 510, the interview data input to the mobile terminal is transmitted from the mobile terminal to the controlling unit. On the basis of the transmitted interview data, the preparation information related to the preparation for the examination of the patient P performed by the medical image diagnosis apparatus is determined, so that the monitor 136 displays the preparation information. In the medical image diagnosis system S1 described herein, the preparation information is at least one of: the posture of the patient P during the examination; the type of the reception coil attached onto the patient P for the examination; and the procedure for attaching the reception coil onto the patient P. Further, in the medical image diagnosis system S1 described herein, on the basis of the preparation information, the location of the reception coil to be attached onto the patient P is indicated from the coil storage shelf storing the plurality of reception coils. With these arrangements, in the medical image diagnosis system S1 described herein, as being triggered by the mounting of the mobile terminal carried by the technologist 1 on the mount unit 510, it is possible to visually and/or auditorily provide the technologist 1 with the preparation information needed by the technologist 1 to prepare, prior to the examinations, for various types of examinations to be performed on the patient P. It is therefore possible to improve work efficiency of the technologist 1.

Fourth Embodiment

In a fourth embodiment, an imaging condition of the examination of the patient P is set on the basis of the input relevant information, so that the monitor 136 displays an instruction to check the imaging condition being set.

Figure 8:
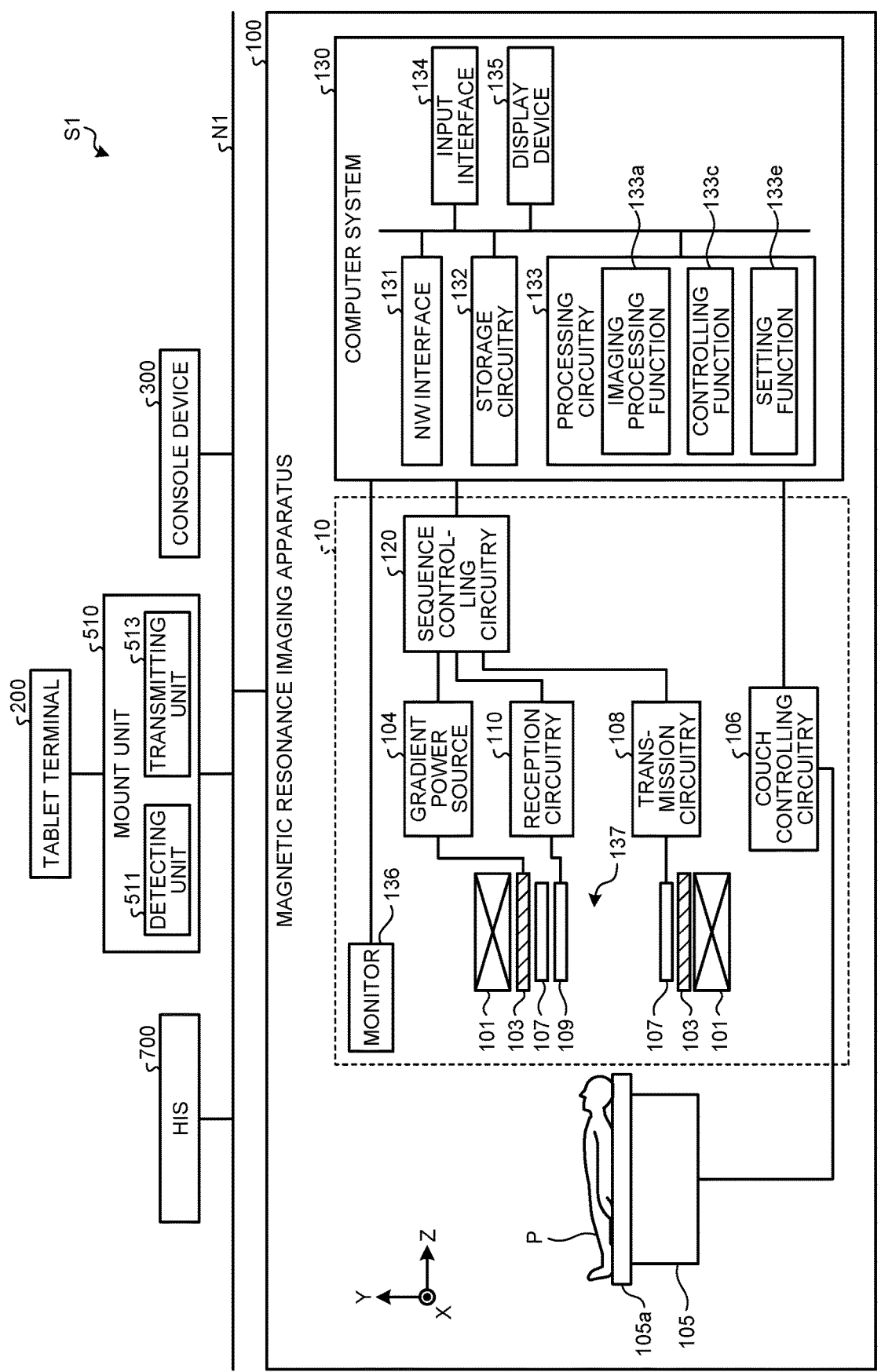
FIG. 8 is a block diagram illustrating an example of the medical image diagnosis system S1 including an MRI apparatus according to a fourth embodiment.

FIG. 8 is a block diagram illustrating an example of the medical image diagnosis system S1 including the MRI apparatus 100 according to the fourth embodiment. In an example, the processing circuitry 133 includes the imaging processing function 133a, the controlling function 133c, and a setting function 133e. The setting function 133e is an example of a setting unit.

The setting function 133e is configured to set the imaging condition of the examination of the patient P, on the basis of the input relevant information. Because the medical image diagnosis apparatus according to the present embodiment is the MRI apparatus 100, the examination of the patient P is an examination using an RF pulse. Accordingly, the imaging condition may be, for example, a condition of an RF pulse emission.

The controlling function 133c is configured to cause the monitor 136 to display the imaging condition set by the setting function 133e, together with an instruction to check the imaging condition. For example, the instruction to check the imaging condition is a character string prompting the technologist 1 to check the set imaging condition and may be presented as a check dialogue box, for instance.

Next, a process (hereinafter, "condition setting checking process") related to setting and checking the imaging condition of the MRI apparatus 100 to be performed by the medical image diagnosis system S1 according to the present embodiment will be explained, with reference to FIG. 9. FIG. 9 is a flowchart illustrating an example of a flow in the condition setting checking process according to the fourth embodiment.

The condition setting checking process:
Step S901:
It is judged whether or not the terminal mount has been detected. More specifically, when the tablet terminal 200 is mounted on the mount base 510, the detecting unit 511 detects the terminal mount (step S901: Yes). In this situation, the process at step S902 will be performed. Because the other aspects of the process are the same as at step S401, the explanations thereof will be omitted.

Step S902:
The input relevant information is transmitted from the tablet terminal 200 to the MRI apparatus 100. More specifically, the transmitting unit 513 transmits the input relevant information from the tablet terminal 200 to the MRI apparatus 100.

Step S903:
On the basis of the input relevant information, an imaging condition of the examination is set. More specifically, by using the weight of the patient P and the height of the patient P in the input relevant information, the setting function 133e sets the imaging condition so that a Specific Absorption Rate (SAR) of the RF pulse emission onto the patient P is lower than a reference value. Further, when the interview data included in the input relevant information indicates that the patient P has a metal implant or the like, the setting function 133e sets the imaging condition by further taking the implant of the patient P into account. Because the method for setting the imaging condition while taking the SAR and the implant into account can follow any of existing methods, the explanations thereof will be omitted.

Step S904:
The monitor 136 displays the imaging condition being set, together with an instruction to check the imaging condition. More specifically, the controlling function 133c causes the monitor 136 to display the imaging condition being set, together with the instruction to check the imaging condition. When an approval is input in response to the instruction to check the imaging condition, the controlling function 133c determines the imaging condition as the imaging condition to be used for the examination of the patient P. The controlling function 133c outputs the determined imaging condition to the sequence controlling circuitry 120. At the present step, the condition setting checking process ends.

In a modification example of the technical concepts of the present embodiment, it is possible to apply, as appropriate, the condition setting checking process illustrated in FIG. 9 to another modality such as an X-ray CT apparatus, an X-ray diagnosis apparatus, or a nuclear medicine diagnosis apparatus. For example, when the examination of the patient P is an examination using X-rays, i.e., when the medical image diagnosis apparatus included in the medical image diagnosis system S1 is an X-ray CT apparatus or an X-ray diagnosis apparatus, the imaging condition of the examination corresponds to a condition of X-ray exposure. In that situation, as the process at step S903, the following processes will be performed, for example.

Step S903:

On the basis of past examination information of the patient P obtained by using the input relevant information and the input relevant information, the setting function 133e sets an imaging condition so that the radiation exposure amount of the patient P caused by the X-ray exposure is smaller than a reference value. More specifically, the setting function 133e extracts the identification data from the input relevant information. For example, the setting function 133e obtains the past examination information of the patient P from an HIS 700 (e.g., an electronic medical record system in the HIS 700) via the network N1, by using the patient ID included in the identification data. The past examination information is, for example, the radiation exposure amount from the X-rays in a past examination of the patient P. The setting function 133e sets an imaging condition (an X-ray tube current and an X-ray tube voltage) on the basis of the radiation exposure amount of the patient P and the height and the weight of the patient P.

In the medical image diagnosis system S1 according to the fourth embodiment described above, when it is detected that the mobile terminal is mounted on the mount unit 510, the input relevant information is transmitted from the mobile terminal to the medical image diagnosis apparatus. The imaging condition of the examination is set on the basis of the transmitted input relevant information, so that the monitor 136 displays the set imaging condition together with the instruction to check the imaging condition. For example, when the examination of the patient P is an examination using an RF pulse, the imaging condition is a condition of the RF pulse emission during the examination. In the medical image diagnosis system S1 described herein, it is possible to set the imaging condition so that the Specific Absorption Rate (SAR) of the RF pulse emission onto the patient P is lower than the reference value, on the basis of the input relevant information. In another example, when the examination of the patient P is an examination using X-rays, the imaging condition is the condition of the X-ray exposure during the examination. In the medical image diagnosis system S1 described herein, on the basis of the past examination information of the patient P obtained by using the input relevant information and the input relevant information, it is possible to set the imaging condition so that the radiation exposure amount of the patient P caused by the X-ray exposure is smaller than the reference value.

With these arrangements, in the medical image diagnosis system S1 according to the fourth embodiment, as being triggered by the mounting of the mobile terminal carried by the technologist 1 on the mount unit 510, the imaging condition is set so that the impact on the patient P is smaller than a reference value, on the basis of the input relevant information and by further using the past examination information depending on the type of the medical image diagnosis apparatus. The monitor 136 is configured to display the imaging condition being set, together with the instruction to check the imaging condition. It is therefore possible to improve work efficiency of the technologist 1 related to setting the imaging condition.

When the technical concepts of any of the first to the fourth embodiments, the modification examples, and the application examples are realized as a medical image diagnosis apparatus controlling program, the medical image diagnosis apparatus controlling program realizes causing a computer to exercise control over a medical image diagnosis apparatus upon receipt of the detection signal indicating that the mobile terminal is mounted on the mount unit 510 capable of having the mobile terminal mounted thereon. Because processing procedures and advantageous effects of the medical image diagnosis apparatus controlling program are the same as those of the first to the fourth embodiments, the modification examples, and the application examples, the explanations thereof will be omitted.

According to at least one aspect of the embodiments and the like described above, it is possible to increase throughput of the examinations, by improving the workflow of the examination of the patient P.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis system, comprising:
   a mount base and/or a holder configured to have a mobile terminal mounted thereon;
   a sensor configured to detect whether or not the mobile terminal is currently mounted on the mount base and/or the holder;
   processing circuitry configured to, in response to determining that the sensor has detected that the mobile terminal is currently mounted on the mount base and/or the holder, exercise control over a medical image diagnosis apparatus; and
   transmission circuitry configured to, in response to determining that the sensor has detected that the mobile terminal is mounted on the mount base, transmit identification data that is included in input relevant information and that makes it possible to identify the patient, from the mobile terminal to the medical image diagnosis apparatus, wherein
   the processing circuitry is further configured to compare the identification data against appointment list data representing an appointment list of examinations performed by the medical image diagnosis apparatus,
   when determining that examination appointment data that is closest in time within the appointment list data matches the identification data, the processing circuitry is further configured to cause a monitor to display the input relevant information, and
   when determining that the examination appointment data and the identification data do not match, the processing circuitry is further configured to cause the monitor to display an instruction to check the input relevant information.

2. The medical image diagnosis system according to claim 1, further comprising:
   the monitor, which is configured to be visually recognizable by a user operating the medical image diagnosis apparatus and the patient examined by the medical image diagnosis apparatus.

3. The medical image diagnosis system according to claim 1, wherein, when determining that the examination appointment data and the identification data do not match, the processing circuitry is further configured to change a sequential order of the examinations in the appointment list so as to prioritize the examination of the patient and cause the monitor to display the input relevant information.

4. The medical image diagnosis system according to claim 1, wherein the processing circuitry is further configured to control a moving mechanism of a movable part included in the medical image diagnosis apparatus so as to change a state of the movable part.

5. The medical image diagnosis system according to claim 4, wherein
the movable part is a couch, and
the state of the movable part is one or both of: (1) elevation of the couch, and (2) a position of a couchtop of the couch.

6. The medical image diagnosis system according to claim 4, wherein
the transmission circuitry is further configured to, in response to determining that the sensor has detected that the mobile terminal is mounted on the mount base and/or the holder, transmit height information of the patient examined by the medical image diagnosis apparatus, from the mobile terminal to the processing circuitry, wherein
the processing circuitry is further configured to control the driving mechanism based on the height information.

7. The medical image diagnosis system according to claim 4, wherein
the movable part is a dockable couch configured to dock onto a gantry including an imaging system related to imaging of the patient examined by the medical image diagnosis apparatus, and
the state of the movable part is whether power of the dockable couch is turned on or off.

8. The medical image diagnosis system according to claim 4, wherein
the movable part is an imaging system related to imaging of the patient examined by the medical image diagnosis apparatus, and
the state of the movable part is whether or not a locked state is achieved in relation to moving of the imaging system.

9. The medical image diagnosis system according to claim 1, wherein
the mobile terminal receives an input of interview data related to interviewing the patient in relation to an examination performed by the medical image diagnosis apparatus,
the transmission circuitry is further configured to, when determining that the sensor has detected that the mobile terminal is mounted on the mount base and/or the holder, transmit the interview data from the mobile terminal to the processing circuitry,
the processing circuitry is further configured to determine preparation information related to preparing for the examination of the patient to be performed by the medical image diagnosis apparatus, based on the interview data, and
the processing circuitry is further configured to cause the monitor to display the preparation information, the monitor being visually recognizable by a user operating the medical image diagnosis apparatus and the patient examined by the medical image diagnosis apparatus.

10. The medical image diagnosis system according to claim 9, wherein the preparation information is at least one of: a posture of the patient during the examination; a type of a reception coil attached onto the patient for the examination; or a procedure for attaching the reception coil onto the patient.

11. The medical image diagnosis system according to claim 10, further comprising an output device configured to, based on the preparation information, indicate a location of the reception coil to be attached onto the patient, from a coil storage shelf storing a plurality of reception coils.

12. The medical image diagnosis system according to claim 1, wherein the transmission circuitry is further configured to, in response to determining that the sensor detected that the mobile terminal is mounted on the mount base and/or the holder, transmit the input relevant information to the mobile terminal regarding the patient examined by the medical image diagnosis apparatus, from the mobile terminal to the medical image diagnosis apparatus, wherein
the processing circuitry is further configured to set an imaging condition of the examination based on the input relevant information, and
the processing circuitry is further configured to cause the imaging condition to be displayed on the monitor, which is visually recognizable by a user operating the medical image diagnosis apparatus, together with an instruction to check the imaging condition.

13. The medical image diagnosis system according to claim 12, wherein
when the examination is an examination using a radio frequency (RF) pulse, the imaging condition is a condition of an RF pulse emission during the examination, and
based on the input relevant information, the processing circuitry is further configured to set the imaging condition so that a Specific Absorption Rate (SAR) of the RF pulse emission onto the patient is lower than a reference value.

14. The medical image diagnosis system according to claim 12, wherein
when the examination is an examination using X-rays, the imaging condition is a condition of X-ray exposure during the examination, and
based on past examination information of the patient, obtained by using the input relevant information, and the input relevant information, the processing circuitry is further configured to set the imaging condition so that a radiation exposure amount of the patient caused by the X-ray exposure is smaller than a reference value.

15. A medical image diagnosis apparatus controlling method, comprising:
detecting, by a sensor, whether or not a mobile terminal is currently mounted on a mount base and/or a holder configured to have the mobile terminal mounted thereon;
exercising control over a medical image diagnosis apparatus, in response to receiving a detection signal indicating that the sensor has detected that the mobile terminal is currently mounted on a mount base and/or the holder;
in response to determining that the sensor has detected that the mobile terminal is mounted on the mount base, transmitting identification data that is included in input relevant information and that makes it possible to identify the patient, from the mobile terminal to the medical image diagnosis apparatus,
comparing the identification data against appointment list data representing an appointment list of examinations performed by the medical image diagnosis apparatus,
when determining that examination appointment data that is closest in time within the appointment list data matches the identification data, causing a monitor to display the input relevant information, and when determining that the examination appointment data and the identification data do not match, causing the monitor to display an instruction to check the input relevant information.

* * * * *